(12) United States Patent
Murata

(10) Patent No.: US 12,400,760 B2
(45) Date of Patent: Aug. 26, 2025

(54) METHOD FOR SELF-DIAGNOSIS AND METHOD FOR SELF-TREATMENT OF POSTERIOR SEGMENT EYE DISEASE

(71) Applicant: Masatoshi Murata, Morioka (JP)

(72) Inventor: Masatoshi Murata, Morioka (JP)

( * ) Notice: Subject to any disclaimer, the term of this patent is extended or adjusted under 35 U.S.C. 154(b) by 630 days.

(21) Appl. No.: 17/872,268

(22) Filed: Jul. 25, 2022

(65) Prior Publication Data

US 2024/0023806 A1 Jan. 25, 2024

(51) Int. Cl.
*G16H 50/20* (2018.01)
*A61B 3/00* (2006.01)

(52) U.S. Cl.
CPC ........... *G16H 50/20* (2018.01); *A61B 3/0033* (2013.01)

(58) Field of Classification Search
CPC ...... G16H 50/20; G16H 30/20; A61B 3/0033; A61F 9/0017
USPC ......................................................... 351/223
See application file for complete search history.

(56) References Cited

U.S. PATENT DOCUMENTS

| | | | |
|---|---|---|---|
| 8,349,005 B2 | 1/2013 | Murata | |
| 9,642,864 B2 | 5/2017 | Murata | |
| 9,788,995 B2 * | 10/2017 | Prausnitz | A61P 27/06 |
| 10,463,532 B2 * | 11/2019 | Murata | A61F 9/0017 |
| 11,723,798 B2 * | 8/2023 | Clem | A61F 9/0008 |
| | | | 604/116 |
| 2010/0226971 A1 * | 9/2010 | Chau | A61K 9/0009 |
| | | | 424/130.1 |
| 2014/0221904 A1 * | 8/2014 | Murata | A61K 31/573 |
| | | | 514/180 |

OTHER PUBLICATIONS

Venkatesh P et al. "Selfie fundus imaging: Innovative approach to retinopathy screening." The National Medical Journal of India 31.6 (2018): 345-346.
Kumari S et al. "Selfie fundus imaging for diabetic retinopathy screening." Eye (2021): 1-6.
Khanamiri HN et al. "Smartphone fundus photography." JoVE (Journal of Visualized Experiments) 125 (2017): e55958.

* cited by examiner

*Primary Examiner* — Mohammed A Hasan
(74) *Attorney, Agent, or Firm* — DZ Buschmann Law

(57) ABSTRACT

Method for self-diagnosis of posterior segment eye disease are provided wherein a patient (a) obtains a self-fundus imageby instilling mydriatic drops to dilate their pupil, placing a monitor that outputs an image captured by a fundus videography camera, placing a lens in front of their eye, holding the camera so that the fundus can be recorded through the lens and focuses the camera, placing a lens in front of their eye, holding the camera so that the fundus can be recorded through the lens and focuses the camera on the fundus of their eye while checking the monitor, recording a video of their fundus with the camera, and obtaining a self-fundus image as a still image from the video, and b) provides the self-fundus image into an automatically constructed deep-learning model to determine whether or not the patient has posterior segment eye disease.

7 Claims, 14 Drawing Sheets

METHOD FOR SELF-DIAGNOSIS AND METHOD FOR SELF-TREATMENT OF POSTERIOR SEGMENT EYE DISEASE

TECHNICAL FIELD

Embodiments described herein generally relate to a method for self-diagnosis and a method for self-treatment of posterior segment eye disease.

BACKGROUND

In recent years, the pandemic of coronavirus disease 19 (COVID-19) has impacted the lives of every individual on a global scale. From the viewpoint of avoiding the spread of COVID-19, it is desirable for physicians, including ophthalmologists, to remotely examine patients. However; accurate tests and diagnoses are difficult to be performed remotely, and even when a disease is found, it is difficult to treat the disease remotely. As a means to solve these problems in the field of ophthalmology, particularly in the posterior segment eye, methods are being sought for the test, diagnosis, and treatment of eye diseases, especially posterior segment eye diseases (PSED), by patients themselves.

In general, fundus test is used to diagnose posterior segment eye disease. Examples of the fundus test include ophthalmoscopy, biomicroscopy, and fundus imaging. In recent years, a method has been reported in which a patient obtains his/her own fundus image, hereinafter referred to as "self-fundus image (SFI)," using a hand-held camera device (Non-Patent Document 1). Such a device is useful for examining patients who are difficult to attend a clinic. However, it is expensive for the patient to purchase the device, and it is not easy to operate the device to obtain a self-fundus image.

RELATED ART DOCUMENTS

Non-Patent Document

[Non-Patent Document 1] Venkatesh P, Kumar S. Tandon N, Takkar B Praveen P A. "Selfie fundus imaging: Innovative approach to retinopathy screening" Natl. Med. J. India 2018 November-December; 31(6): 345-346.

Therefore, the present inventor focused on a camera of a smart device such as a smart phone widely distributed, and considered to obtain a self-fundus image of a patient by a simple operation without requiring an expensive device. Furthermore, the present inventor found that by providing the obtained self-fundus image of the patient into an automatically constructed deep-learning model to determine whether or not the patient has posterior segment eye disease, the patient him/herself can accurately perform self-test and diagnosis of eye disease, in particular, posterior segment eye disease (PSED).

In addition, the present inventor considered the possibility of patients treating the eye disease by himself/herself when the patient is diagnosed as having eye disease. In the case when the patient performs self-treatment, e.g. self-treatment of PSED, it is difficult for patients to deliver effective doses of drugs to the posterior segment eye (PSE), especially disc-macular area for a long period of time. Systemic administration requires large doses of drugs and may cause various side effects. When topical eye drops are used, penetration into PSE is difficult because of the long diffusion path length, lacrimation, and impermeability of cornea. In the case of intravitreal injection, an operation by ophthalmologist is required and must be repeated to maintain the therapeutic level of the drugs, and there is a potential risk of glaucoma, cataract, retinal detachment, and endophthalmitis.

Insertion of a tube for drug injection into an affected area is used in various medical fields including ophthalmology. For example, the drug can be delivered to the PSE by inserting a tube into the pars plana of vitreous body. While this procedure is effective in maintaining the drug concentration in the PSE by using a micropump, it is difficult to accurately deliver the drug only to the disc-macula area.

The present inventor focused on inserting a tube into the choroid to reduce tissue damage and to maintain the drug concentration at an effective level in the PSE, particularly in the disc-macula area. In this case, it is also possible for the patient to inject the drug repeatedly from the outside of the skin through the tube in a simple manner by using the injector Therefore, the present inventor found that a patient diagnosed as having eye disease by the self-test and diagnosis is examined by a physician using a remote communication system, and when the treatment is judged to be necessary, after undergoing tube insertion procedure into the choroid by the physician, the patient him/herself injects a drug into the choroid through the tube inserted, wherein enabling the self-treatment of the posterior segment eye disease.

SUMMARY OF THE INVENTION

That is, it is an object of the present invention to provide a method for self-diagnosis of posterior segment eye diseases that does not require an expensive device, is simple to operate, and accurate, and a method for self-treatment of posterior segment eye diseases in which the potential risk of side effects.

According to the present invention, the following method for self-diagnosis of posterior segment eye disease and the like can be provided.

1. A method for self-diagnosis of posterior segment eye disease, comprising:
    (a) a patient obtains a self-fundus image; and
    (b) the patient provides the self-fundus image into an automatically constructed deep-learning model to determine whether or not the patient has posterior segment eye disease,
    wherein the step (a) comprises:
    (a-1) the patient instills mydriatic drops to dilate his/her pupil;
    (a-2) the patient places a monitor that outputs an image captured by a fundus videography camera;
    (a-3) the patient places a lens in front of his/her eye;
    (a-4) the patient holds the camera so that the fundus can be recorded through the lens and focuses the camera on the fundus of his/her eye while checking on the monitor;
    (a-5) the patient records a video of his/her fundus with the camera; and
    (a-6) the patient obtains a self-fundus image as a still image from the video.
2. The method for self-diagnosis according to 1, wherein the posterior segment eye disease is selected from the group consisting of vitreous opacity, diabetic retinopathy, macular degeneration, retinal vein occlusion, and uveitis.
3. The method for self-diagnosis according to 1, wherein the camera is a smartphone or tablet computer.

4. The method for self-diagnosis according to 1, wherein the monitor is a smartphone or tablet computer.
5. The method for self-diagnosis according to 1, wherein in the step (b), fundus images obtained from the patient with the posterior segment eye disease and fundus images obtained from the patient without the posterior segment eye disease are provided into an exploration framework of neural architecture to automatically construct a deep-learning model.
6. A method for self-treatment of posterior segment eye disease, comprising:
   (d) in a clinic, the physician places one end of a tube for drug injection in a choroid of the patient diagnosed as having posterior segment eye disease by the method for self-diagnosis according to 1 and exposes the other end of the tube outside a skin of the patient; and
   (e) under a remote guidance of the physician, the patient injects a drug into the choroid through the tube inserted into the choroid,
   wherein the step (d) comprises:
   (d-1) incising a conjunctiva, and inserting an injection needle between the conjunctiva and a sclera;
   (d-2) advancing a tip of the injection needle to a vicinity of an optic disc along a surface of the sclera, placing a lens over a cornea so that a fundus can be observed, and observing the tip of the injection needle that can be observed as a white raised portion of the sclera while pressing the sclera using the tip of the injection needle and observing the fundus through the lens;
   (d-3) moving the tip of the injection needle to determine an appropriate insertion position of the tube in the vicinity of the optic disc;
   (d-4) inserting the tip of the injection needle diagonally into the sclera, advancing the tip of the injection needle into the choroid, and inserting the one end of the tube into the choroid through an inlet of the tip of the injection needle; and
   (d-5) placing the one end of the tube into the choroid and pulling out the injection needle.
7. The method for self-treatment according to 6, wherein the step (d) comprises:
   (d-0) placing an implant having a magnet in a scleral pocket or suprachoroidal space.

The present invention provides a method for self-diagnosis of posterior segment eye diseases that does not require an expensive device, is simple to operate, and accurate, and a method for self-treatment of posterior segment eye diseases in which the potential risk of side effects and other eye diseases is low.

DETAILED DESCRIPTION OF THE INVENTION

Embodiments of the method for self-diagnosis and the method for self-treatment of posterior segment eye disease of the present invention will be described below in detail with reference to Drawings. The structure of the eye is described below with reference to FIG. 1. The upper side in FIG. 1, i.e., the side where the cornea is present, is referred to as the anterior side in the structure of the eye, and the lower side in FIG. 1, i.e., the side where the optic nerve is present, is referred to as the posterior side in the structure of the eye.

[Structure of Eye]

Figure 1:
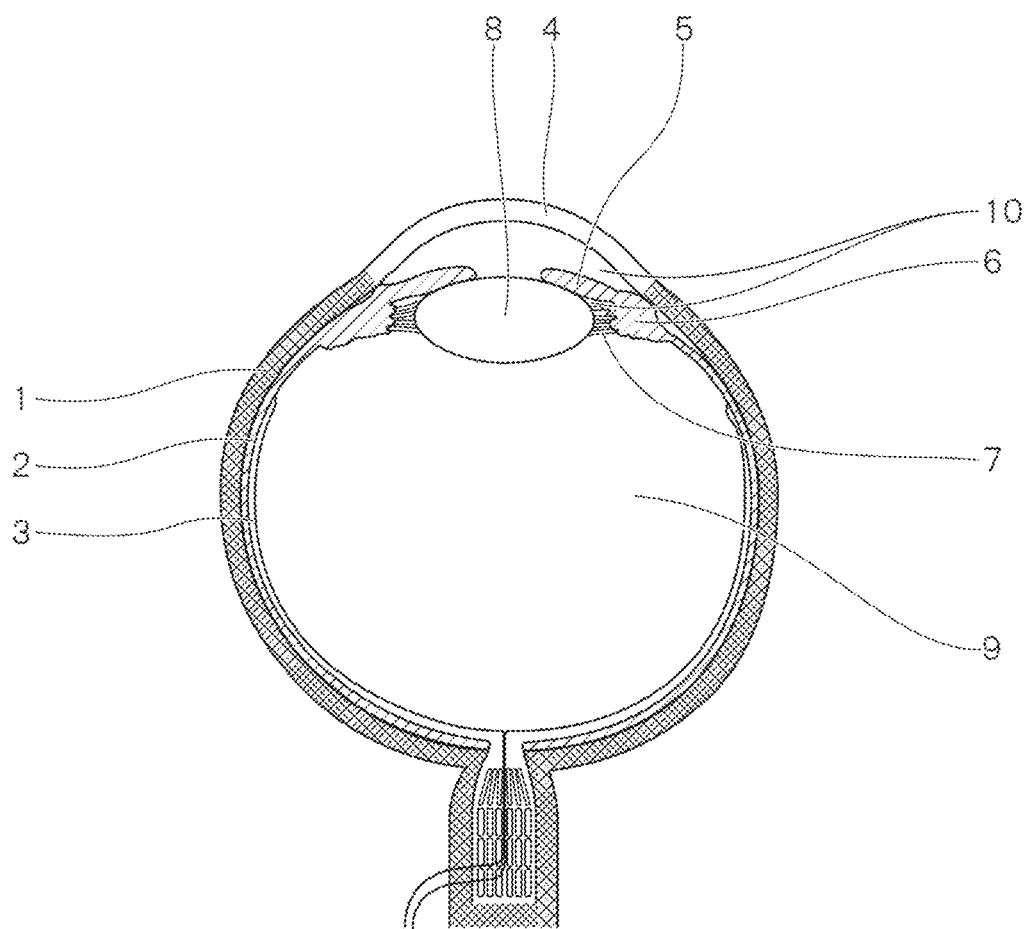
FIG. 1 is a schematic diagram showing the structure of a human eye.

An eye includes an eyeball, adnexa, and optic nerves. As illustrated in FIG. 1, the eyeball contains outer wall members such as a sclera 1, a choroid 2, a retina 3, a cornea 4, an iris 5, a ciliary body 6, and a zonule of Zinn 7, and content members such as a crystalline lens 8, a vitreous body 9, and an aqueous humor 10. The adnexa contain a lacrimal apparatus, a conjunctiva, and the like.

The sclera 1 is a milky white, hard membrane. The anterior end of the sclera 1 is connected to the cornea. The sclera 1 allows light to pass through to only a small extent, and prevents the entry of unnecessary light into the eyeball. The sclera 1 thus protects the inside of the eyeball. The sclera 1 has a thickness of about 1.0 mm to about 1.5 mm in an area in which the sclera 1 forms the rear wall of the eyeball, and has a minimum thickness of about 0.5 mm in an area in which the eye muscle adheres to the sclera 1.

The choroid 2 is a thin blackish brown membrane that is situated between the sclera 1 (that is situated on the outer side) and the retina 3 (that is situated on the inner side). A number of blood vessels are present in the choroid 2, and supply nutrients to the outer layer of the retina in which blood vessels are not present. The thickness of the choroid 2 is about 0.2 mm to about 0.3 mm.

The retina 3 is a thin membrane that includes ten layers. The retina 3 has a thickness of about 0.3 mm to about 0.4 mm in the center area, and has a thickness of about 0.15 mm in the peripheral area. Two types of photoreceptor cells (rod cells and cones) are present in the retina 3. Important cells such as ganglion cells and Mueller cells and a number of blood vessels are also present in the retina 3. A macular area in which a number of cones are present is situated at the center of the rear part of the retina 3. The macular area is part of the eyeball that has the best visual acuity.

The vitreous body 9 is a colorless and transparent gel with which most of the interior of the eyeball is filled. Water accounts for 99% of the vitreous body 9. The vitreous body 9 is situated behind the crystalline lens. The vitreous body 9 is bonded to the retina 3 in a deep area of the eyeball, but most of the vitreous body 9 comes in light contact with the retina 3.

[Posterior Segment Eye Disease]

In FIG. 1, the portion from the posterior side of the crystalline lens 8 to the optic disc is referred to as a posterior segment eye. The outer wall of the posterior segment eye has a three-layer structure in which the sclera 1 forms an outer layer, the choroid 2 forms an intermediate layer, and the retina 3 forms an inner layer.

Posterior segment eye diseases include all eye diseases that occur in the posterior segment eye. That is, posterior segment eye diseases include eye diseases that occur in the sclera 1, choroid 2, retina 3, and vitreous body 9.

Posterior segment eye diseases include, but are not limited to, vitreous opacity, diabetic retinopathy, macular degeneration, retinal vein occlusion, uveitis, and the like.

In one embodiment, the posterior segment eye disease is vitreous opacity.

Vitreous opacity is a disease in which the vitreous body, which is usually clear and colorless, becomes turbid. Light that should nominally reach the retina is blocked by the turbidity, resulting in such symptoms as flying mosquitoes, blurred vision, and decreased visual acuity. The opacity of vitreous may result from infection, inflammation, and hemorrhage, and may also be a malignant disease, the so-called mask syndrome. As the opacity of vitreous progresses, it is difficult to identify the cause by conventional fundus tests due to the opacity, and ultrasonic tomography and diagnostic vitreous biopsy are performed.

If the vitreous opacity can be detected at an early stage by the method for self-diagnosis of the present invention, the cause can be identified, and the burden on the patient can be reduced.

In one embodiment, the posterior segment eye disease is uveitis.

The uvea is a generic term for the iris, ciliary body, and choroid. Inflammation of these tissues is called uveitis. Uveitis also spreads inflammatory to periphery tissues, causing symptoms such as decreased visual acuity. Uveitis may cause vitreous opacity, and as the same as vitreous opacity, early detection may reduce the burden on patients.

Next, a method for self-diagnosis of posterior segment eye disease will be described.

[Method for Self-Diagnosis of Posterior Segment Eye Disease]

The method for self-diagnosis of posterior segment eye disease according to an aspect of the present invention contains (a) a patient obtains a self-fundus image (hereinafter also referred to as "step (a)"), and (b) the patient provides the self-fundus image into an automatically constructed deep-learning model to determine whether or not the patient has posterior segment eye disease (hereinafter, also referred to as "step (b)").

The method for self-diagnosis of posterior segment eye disease according to an aspect of the present invention does not require an expensive device, and patients can independently and accurately diagnose posterior segment eye diseases with a simple operation.

[(a) a Patient Obtains a Self-Fundus Image]

In the method for self-diagnosis of posterior segment eye disease according to an aspect of the present invention, step (a) contains:

(a-1) the patient instills mydriatic drops to dilate his/her pupil (hereinafter also referred to as "step (a-1)");

(a-2) the patient places a monitor that outputs an image captured by a fundus videography camera (hereinafter also referred to as "step (a-2)");

(a-3) the patient places a lens in front of his/her eye (also referred to as "step (a-3)");

(a-4) the patient holds the camera so that the fundus can be recorded through the lens and focuses the camera on the fundus of his/her eye while checking on the monitor (hereinafter also referred to as "step (a-4)");

(a-5) the patient records a video of his/her fundus with the camera (hereinafter also referred to as "step (a-5)"; and (a-6) the patient obtains a self-fundus image as a still image from the video (hereinafter, also referred to as "step (a-6)").

In the step (a-1), the patient instills the mydriatic agent him/herself. As a result, the pupil is dilated and recording of the fundus is facilitated.

The mydriatic agent is not limited as long as it is used in the field of ophthalmology, and examples thereof include tropicamide.

In the step (a-2), the patient places a monitor that outputs the image captured by a fundus videography camera.

As the fundus videography camera, a smartphone or a tablet computer can be used, for example, but the camera is not limited thereto.

As the monitor that outputs an image captured by the fundus videography camera, for example, a smartphone or a tablet computer can be used, but the monitor is not limited thereto.

In the step (a-3), the patient places a lens in front of his/her eye. As the lens, it is preferable to use a lens having a magnification and a field of view sufficient for recording the fundus using the fundus videography camera. For example, 20D lens used in diagnostics in general ophthalmological clinic can be used by placing 5 cm anterior to the eye, but the lens is not limited thereto. The lens may be a lens possessed by the fundus videography camera itself.

In the step (a-4), the patient holds the fundus videography camera so that the fundus can be recorded through the lens and focuses the camera on the fundus of his/her eye while checking on the monitor.

Figure 2:
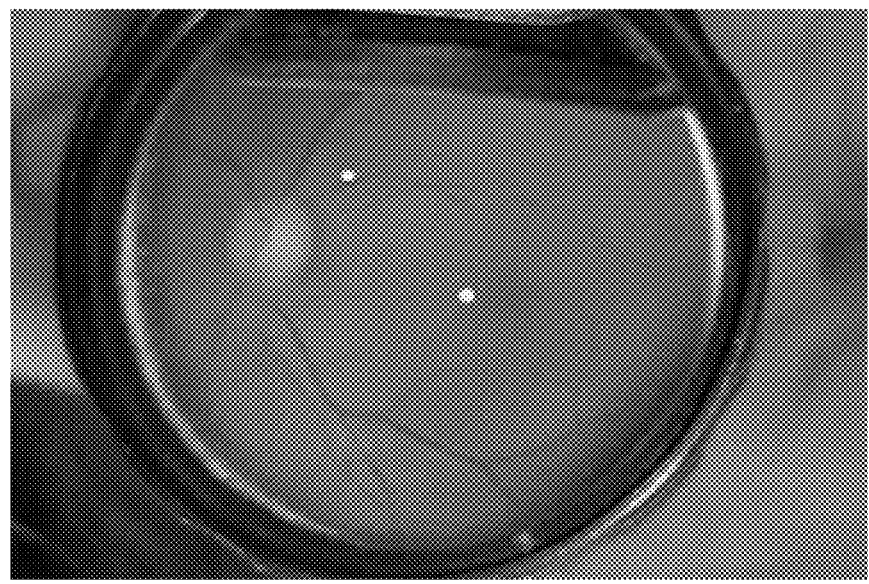
FIG. 2 shows a fundus image obtained in Example.

In the step (a-5), the patient records a video of his/her fundus with the camera In the step (a-6), the patient obtains a self-fundus image as a still image from the video recorded in the step (a-5). The self-fundus image obtained in the step (a) in Example is shown in FIG. 2 as an example.

[(b) the Patient Provides the Self-Fundus Image into an Automatically Constructed Deep-Learning Model to Determine Whether or not the Patient has Posterior Segment Eye Disease]

In the method for self-diagnosis of posterior segment eye disease according to an aspect of the present invention, the step (b) does not require an expensive device, and enables the determination of whether or not the patient has posterior segment eye disease with simple operation and accuracy.

In one embodiment, the step (b) contains:
  (b-1) automatically constructing a deep-learning model for diagnosis of posterior segment eye disease using fundus images obtained from patients having posterior segment eye disease and fundus images obtained from patients not having posterior segment eye disease (hereinafter also referred to as "step (b-1)"); and
  (b-2) the patient provides the self-fundus image obtained in the step (a) into the constructed deep-learning model to determine whether or not the patient has posterior segment eye disease (hereinafter, also referred to as the "step (b-2)").

The method of automatically constructing a deep-learning model is not particularly limited, and the number of images to be used, the model, the number of layers of the model, and the like can be appropriately selected based on a known technique. Various deep neural networks can be used for model construction, for example convolutional neural networks. Various existing services, such as AutoML, may be used to construct models.

In one embodiment, the step (b-1) is providing a search framework of neural architecture with fundus images obtained from patients having posterior segment eye disease and fundus images obtained from patients not having posterior segment eye disease to automatically construct a deep-learning model. In the step (b-2), this model can be used to determine from the self-fundus image whether the patient has posterior segment eye disease.

In one embodiment, the step (b-1) is providing a search framework of neural architecture with fundus images obtained from patients having vitreous opacity and fundus images obtained from patients not having vitreous opacity to automatically construct a deep-learning model. In the step (b-2), this model can be used to determine from the self-fundus image whether the patient has vitreous opacity.

Next, a method for self-treatment of posterior segment eye disease will be described.

[Method for Self-Treatment of Posterior Segment Eye Disease]

The method for self-treatment of posterior segment eye disease according to an aspect of the present invention contains
  (d) in a clinic, the physician places one end of a tube for drug injection in a choroid of the patient diagnosed as having posterior segment eye disease by the method for self-diagnosis according to an aspect of the present invention and exposes the other end of the tube outside a skin of the patient (hereinafter also referred to as "step (d)"); and
  (e) under a remote guidance of the physician, the patient injects a drug into the choroid through the tube inserted into the choroid (hereinafter also referred to as "step (e)").

The method for self-treatment of posterior segment eye disease according to an aspect of the present invention may contain:
  (c) the patient diagnosed as having posterior segment eye disease by the method for self-diagnosis according to an aspect of the present invention is examined by a physician using a remote communication system (hereinafter, also referred to as "step (c)").

[(c) the Patient Diagnosed as Having Posterior Segment Eye Disease by the Method for Self-Diagnosis According to an Aspect of the Present Invention is Examined by a Physician Using a Remote Communication System]

In the method for self-treatment of posterior segment eye disease according to an aspect of the present invention, the step (c) enables accurate diagnosis using a remote communication system on the basis of information obtained by the self-diagnosis in the steps (a) and (b) described above, even if the physician performing a diagnosis remotely.

[(d) in a Clinic, the Physician Places One End of a Tube for Drug Injection in a Choroid of the Patient and Exposes the Other End of the Tube Outside a Skin of the Patient]

In the method for self-treatment of posterior segment eye disease according to an aspect of the present invention, the step (d) enables a physician to place one end of a tube for drug injection in the choroid of a patient in a clinic, thereby enabling a method for self-treatment of posterior segment eye disease in which the patient can inject a drug into the choroid via a tube inserted therein and reduce the potential risk of side effects and other eye diseases. Further, by exposing the other end of the tube to the outside of the skin, the drug can be easily and repeatedly injected. The physician may examine the patient in the step (d) before the step (d-1).

In the following embodiments and Examples, the tube is placed in the choroid, but the tube may be placed in the suprachoroidal space. Even when the tube was placed on the suprachoroidal space, tissue damage can be reduced and the concentration of the drug in the region of the PSE, particularly from the disc-macula area, can be maintained at an effective level, as when the tube is placed in the choroid.

In the method for self-treatment of posterior segment eye disease according to an aspect of the present invention, the step (d) contains
  (d-1) incising a conjunctiva, and inserting an injection needle between the conjunctiva and a sclera (hereinafter also referred to as "step (d-1)");
  (d-2) advancing a tip of the injection needle to a vicinity of an optic disc along a surface of the sclera, placing a lens over a cornea so that a fundus can be observed, and observing the tip of the injection needle that can be observed as a white raised portion of the sclera while pressing the sclera using the tip of the injection needle and observing the fundus through the lens (hereinafter also referred to as "step (d-2)");

(d-3) moving the tip of the injection needle to determine an appropriate insertion position of the tube in the vicinity of the optic disc (hereinafter also referred to as "step (d-3)");

(d-4) inserting the tip of the injection needle diagonally into the sclera, advancing the tip of the injection needle into the choroid, and inserting the one end of the tube into the choroid through an inlet of the tip of the injection needle (hereinafter also referred to as "step (d-4)"); and (d-5) placing the one end of the tube into the choroid and pulling out the injection needle (hereinafter also referred to as "step (d-5)").

A method of inserting the tube for drug injection in the step (d) will be described with reference to the Drawings.

It should be noted that the present invention is not limited to the specific matters described in the following embodiments and Examples as long as the method contains incising a conjunctiva, and inserting an injection needle between the conjunctiva and a sclera; advancing a tip of the injection needle to a vicinity of an optic disc along a surface of the sclera, placing a lens over a cornea so that a fundus can be observed, and observing the tip of the injection needle that can be observed as a white raised portion of the sclera while pressing the sclera using the tip of the injection needle and observing the fundus through the lens; determining an appropriate insertion position of the tube in the vicinity of the optic disc; inserting the tip of the injection needle diagonally into the sclera, advancing the tip of the injection needle into the choroid, and inserting the tube into the choroid through an inlet of the tip of the injection needle. In addition, in some Examples described below, the rabbit is used as an object to be treated, but the present invention can be applied to humans in the same manner.

As the tube for drug injection, those used in various medical fields including ophthalmology can be used. As the tube for drug injection, for example, a silicon tube can be used.

Figure 3:
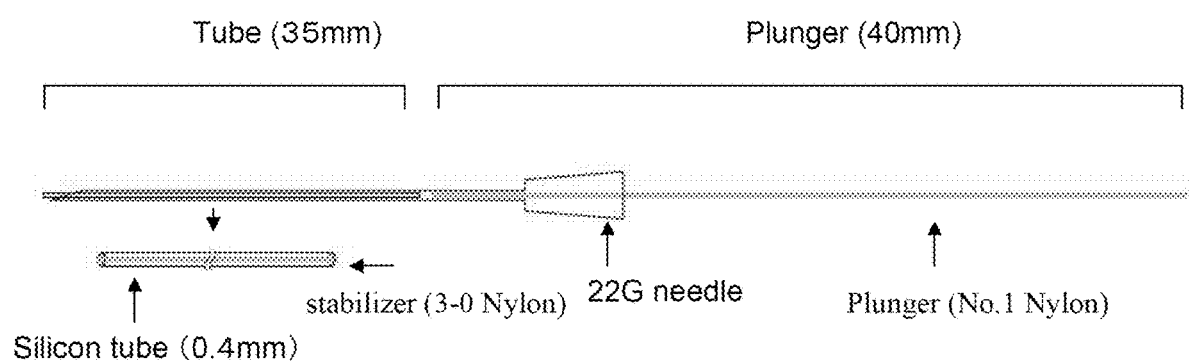
FIG. 3 is a schematic diagram illustrating an example of a tube insertion system used in the step of placing one end of the tube for drug injection into the choroid in a method for self-treatment according to an aspect of the present invention.
Figure 4A:
FIG. 4 shows a photograph of a tube insertion system used in the step of placing one end of the tube for drug injection into the choroid in a method for self-treatment according to an aspect of the present invention.
Figure 4B:
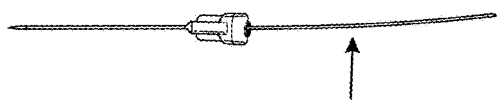
Figure 4C:
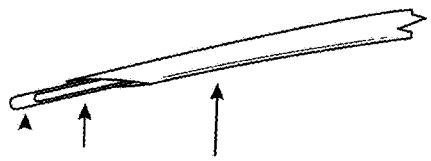
Figure 4D:
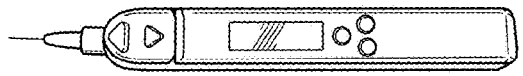

In the method of inserting the tube for drug injection, a tube insertion system configured to insert a 3-0 nylon (e.g., length: 35 mm) into a 0.4 mm silicone tube (e.g., length: 35 mm), insert the 0.4 mm silicone tube into a 22 G needle, and insert a No. 1 nylon into the needle from the rear of the needle, as shown in FIG. 3, can be suitably used. The No. 1 nylon pushes the tube as an implant out of the needle tip as a plunger. Also, the 3-0 nylon serves as an inner stabilizer to support the tube and insert the tube into the choroid. The dimensions of the tube, the injection needle, the plunger, and the inner stabilizer are not limited to the above combinations, and can be freely selected as long as the purpose of inserting the tube into the choroid is achieved. In this specification, the configuration of the tube insertion system shown in FIG. 3 will be used for explanation.

It is preferable to use nylon as a material for forming the plunger, for example. When a wire is used as the plunger, it may be difficult to push the plunger along the curved injection needle since the plunger may be caught in the curved injection needle due to too high a hardness. When a silk thread is used as the plunger, the plunger can be pushed along the curved injection needle, but it may be difficult to push the tube forward due to too high a softness. Since nylon has moderate hardness and elasticity, nylon is suitable as the material for forming the plunger. Note that the material of the plunger is not limited to nylon, and any material having the same hardness can be suitably used as in the case of nylon.

The plunger can be moved manually, for example by pushing the rear end of the plunger with a finger. The injector can also be used to move the plunger wirelessly. After insertion of the tube, the injector can also be used to wirelessly inject drug solution into the choroid. For example, a pen-type electric dispenser manufactured by ICOMES LAB Co. Ltd. may suitably be used as the injector.

Figure 5:
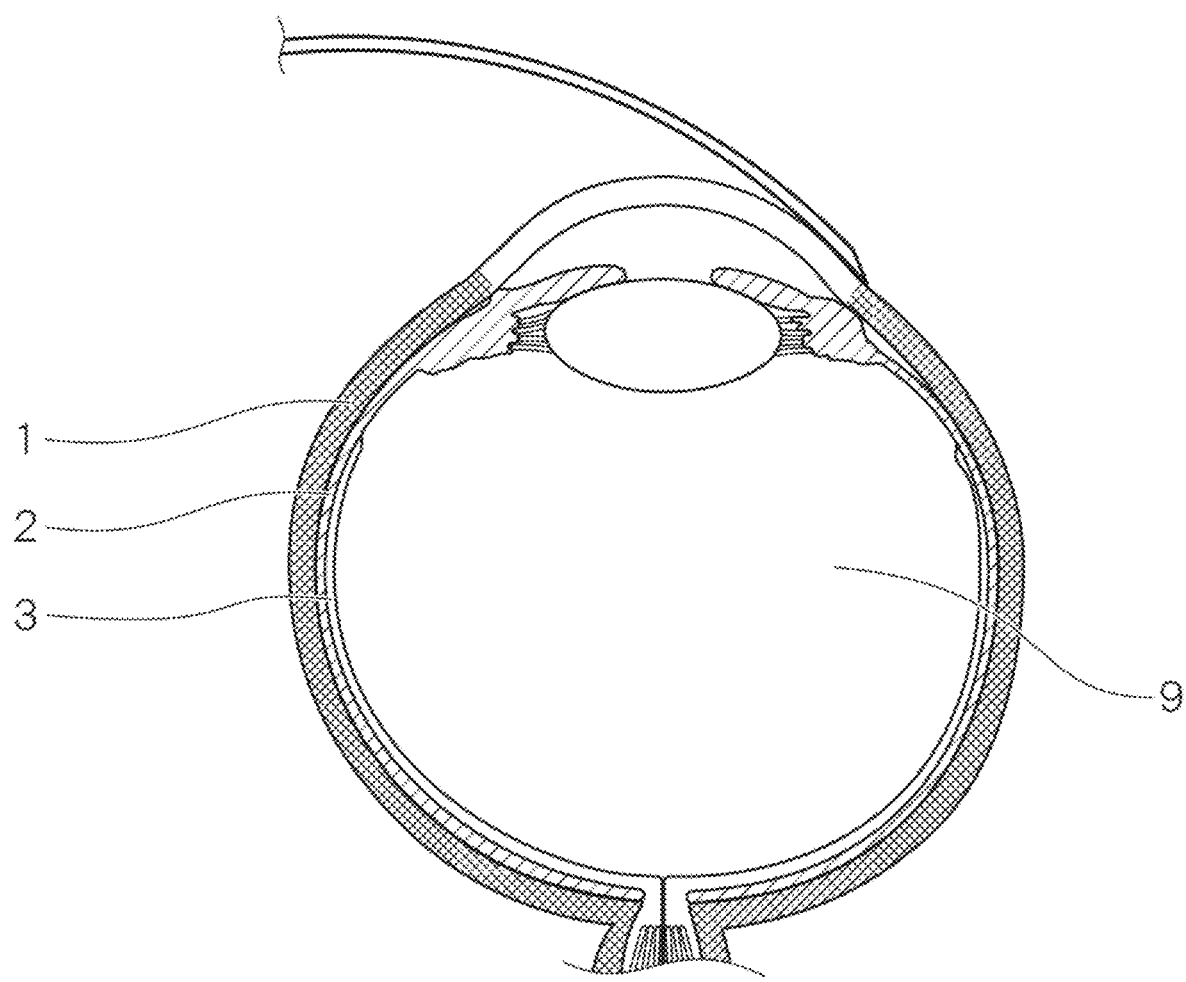
FIG. 5 is a schematic diagram illustrating a state in which a conjunctiva is incised, and an injection needle is inserted between the conjunctiva and the sclera in a method for self-treatment according to an aspect of the present invention (the conjunctiva is omitted).
Figure 6:
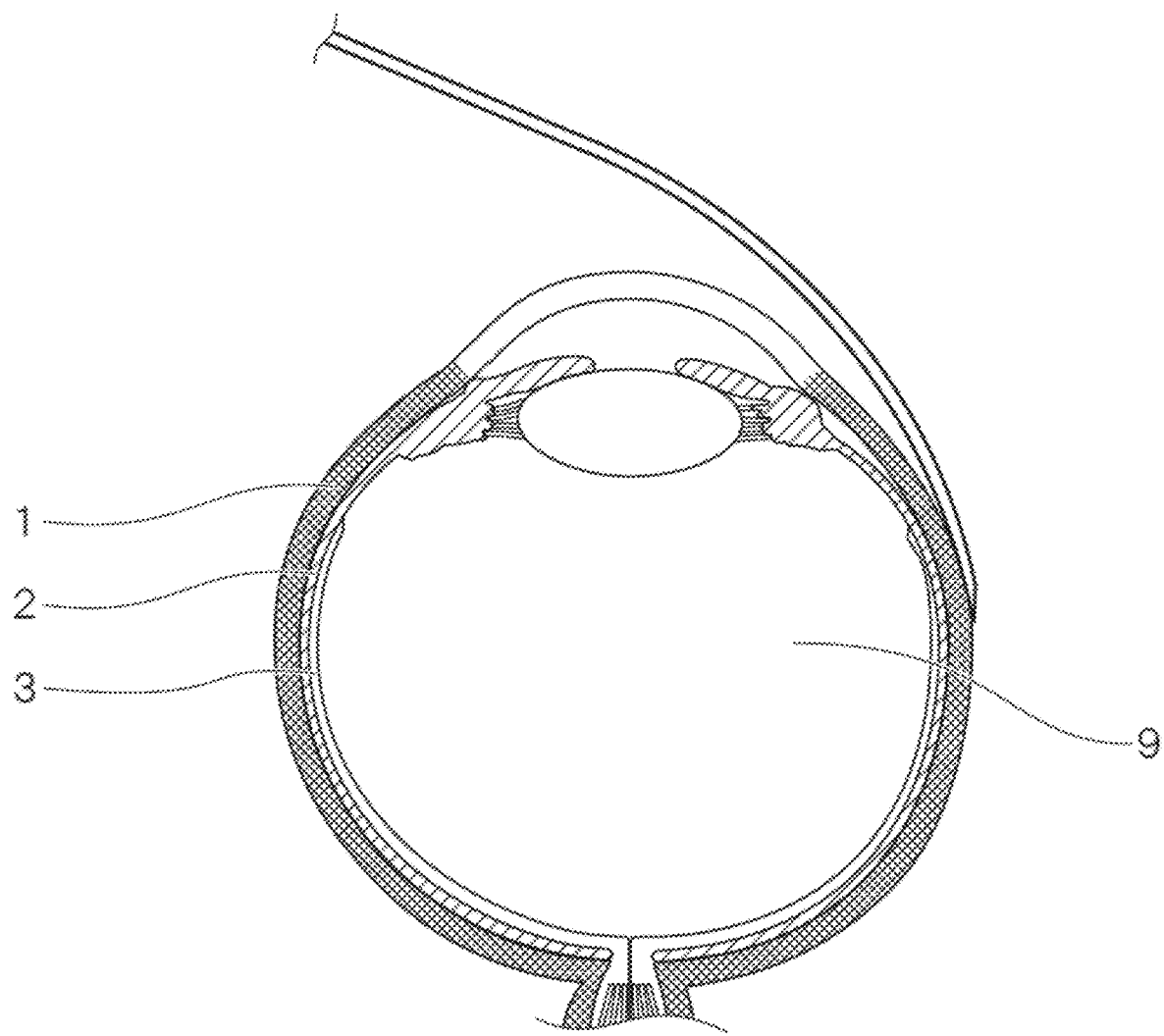
FIG. 6 is a schematic diagram illustrating a state in which the tip of an injection needle is advanced along the surface of the sclera in a method for self-treatment according to an aspect of the present invention.

FIG. 4 shows a photograph of a silicone tube (short arrow) and an inner stabilizer (long arrow) (FIG. 4A); a photograph of a tube insertion system consisting of a tube, an injection needle, and a plunger (arrow) (FIG. 4B); an enlarged photograph of a tip of a needle in which a tube (arrowhead), an inner stabilizer (short arrow), and an injection needle (long arrow) are visible (FIG. 4C); and a photograph of an injector for injecting drug solution into the choroid (FIG. 4D) used in the method for self-treatment of posterior segment eye disease according to an aspect of the present invention (1) Inserting Step of Injection Needle As illustrated in FIGS. 5 and 6, the conjunctiva that covers the eyeball is incised, and an injection needle is inserted between the conjunctiva and the sclera.

An injection needle in which the main body is gently curved, as illustrated in FIGS. 5 and 6, may suitably be used as the injection needle. By curving the main body of the needle in this manner, the injection needle can be inserted between the conjunctiva and the sclera, and the tip of the injection needle can be moved to the vicinity of the optic disc. It is preferable that the injection needle have a size as small as possible from the viewpoint of invasiveness. From such viewpoint, it is preferable that the outer diameter of the main body of the injection needle is 1.0 mm or smaller, 0.9 mm or smaller, or 0.8 mm or smaller. The inner diameter of the main body of the injection needle is preferably 0.7 mm or smaller, 0.6 mm or smaller, or 0.5 mm or smaller. The size of the needle is preferably 22G, 23G, 24G, or 25G, and it is more preferable if an injection needle having a smaller size can be used.

(2) Determining Step of Insertion Position of Tube

Figure 7:
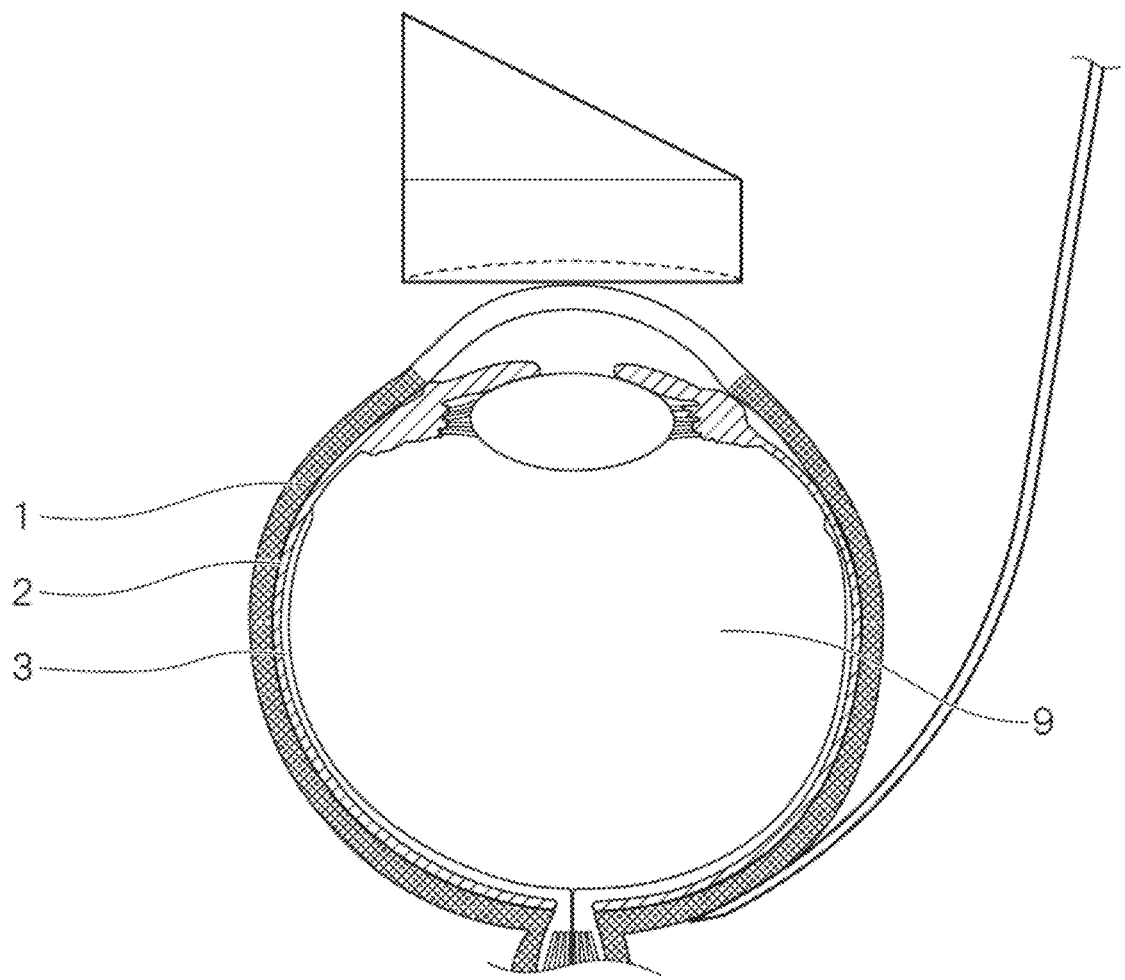
FIG. 7 is a schematic diagram illustrating a state in which the tip of an injection needle is advanced to the vicinity of the optic disc along the surface of the sclera, and a lens is placed over the cornea so that the fundus can be observed in a method for self-treatment according to an aspect of the present invention.

As illustrated in FIG. 7, the tip of the injection needle is advanced to the vicinity of the optic disc along the surface of the sclera. The insertion position of the tube is determined by placing a lens over the cornea such that the fundus can be observed, and observing the tip of the injection needle that can be observed as a white raised portion of the sclera while pressing the sclera using the tip of the injection needle and observing the fundus through the lens.

At this time, the state of the sclera is observed through the retinal side with a lens while pressing the sclera using the tip of the injection needle, and the surface of the sclera that is contiguous to an area of the choroid in the vicinity of the optic disc in which the number of blood vessels is small and a large vessel is not present, is determined to be the insertion position of the tube.

(3) Inserting Step of Injection Needle into Choroid

Figure 8:
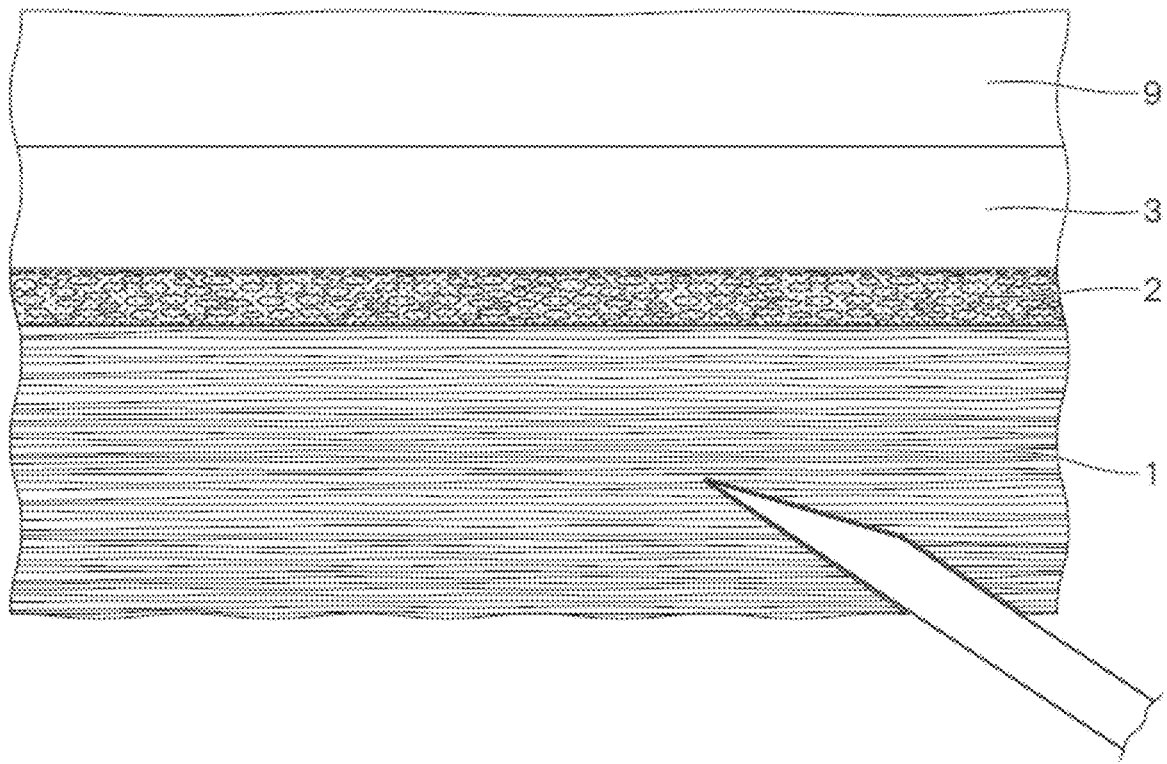
FIG. 8 is an enlarged schematic diagram illustrating a state in which the tip of an injection needle is diagonally inserted into the sclera in a method for self-treatment according to an aspect of the present invention.
Figure 9:
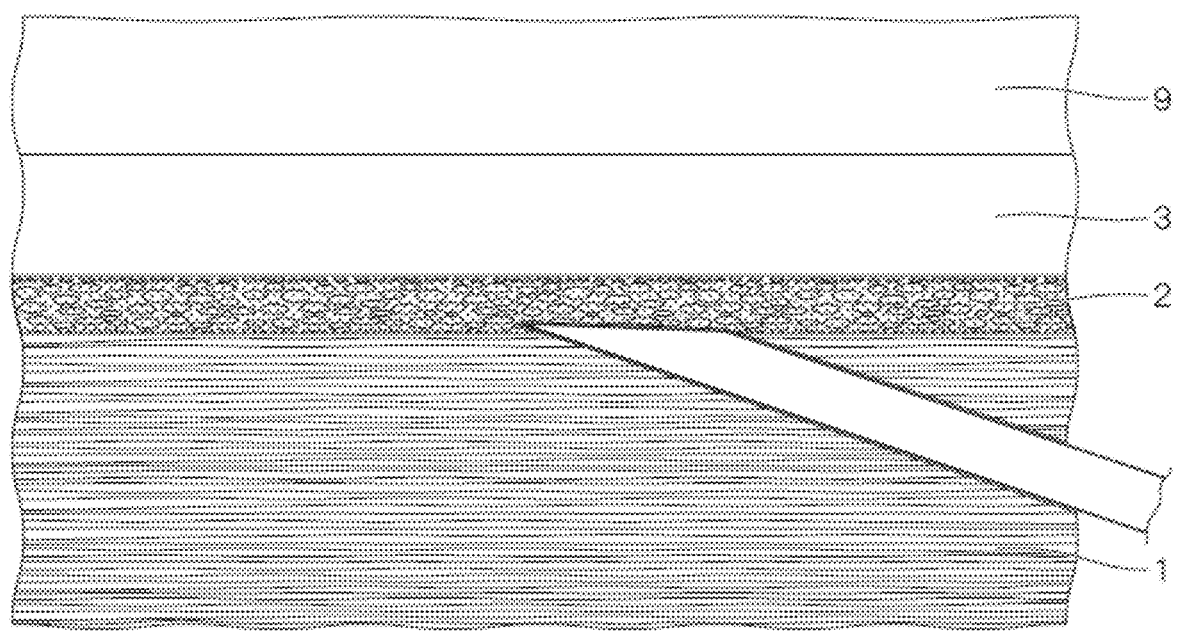
FIG. 9 is an enlarged schematic diagram illustrating a state in which the tip of an injection needle is diagonally inserted into the choroid in a method for self-treatment according to an aspect of the present invention.
Figure 10:
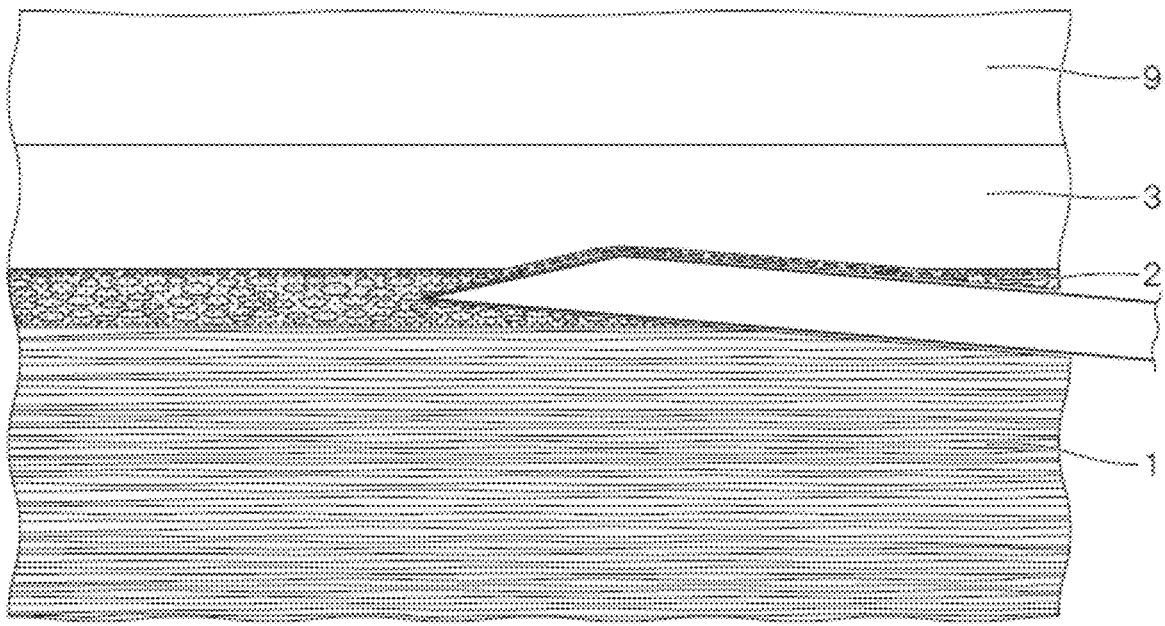
FIG. 10 is an enlarged schematic diagram illustrating a state in which the tip of an injection needle is advanced within the choroid in a method for self-treatment according to an aspect of the present invention.

As illustrated in FIG. 8, the tip of the injection needle is diagonally inserted into the sclera. As illustrated in FIGS. 9 and 10, the tip of the injection needle is then advanced into the choroid.

The insertion of the tip of the injection needle is confirmed by observing the fundus through the lens.

It is determined that the tip of the injection needle has been inserted into the choroid when a state in which the tip of the injection needle is observed through a thick membrane (i.e., an area of the sclera pressed by the tip of the injection needle is observed to be a white area) has changed to a state in which the tip of the injection needle is observed through a thin membrane (i.e., the tip of the injection needle is clearly observed under the retina having a small thickness) when observed through the lens.

Specifically, since the sclera allows light to pass through to only a small extent, the tip of the injection needle is situated under or within the sclera in a state in which the tip of the injection needle is observed through a thick membrane. On the other hand, the tip of the injection needle is situated under the retina and over the sclera in a state in which the tip of the injection needle is observed through a thin membrane. According to, it can be determined that the tip of the injection needle has been inserted into the choroid when the tip of the injection needle is observed through a thin membrane.

After confirming the insertion of the tip of the injection needle into the choroid, the tip of the injection needle is advanced within the choroid parallel to the choroid. Specifically, the tip of the injection needle is moved parallel to (in the tangential direction with respect to) the layer that forms the choroid.

The tip of the injection needle is advanced within the choroid parallel to the choroid until it is observed through the lens that the inlet of the tip of the injection needle has been inserted into the choroid. It is determined that the inlet of the tip of the injection needle has been inserted into the choroid when the inlet of the tip of the injection needle can be observed through a thin membrane.

(4) Insertion Step of Tube

Figure 11:
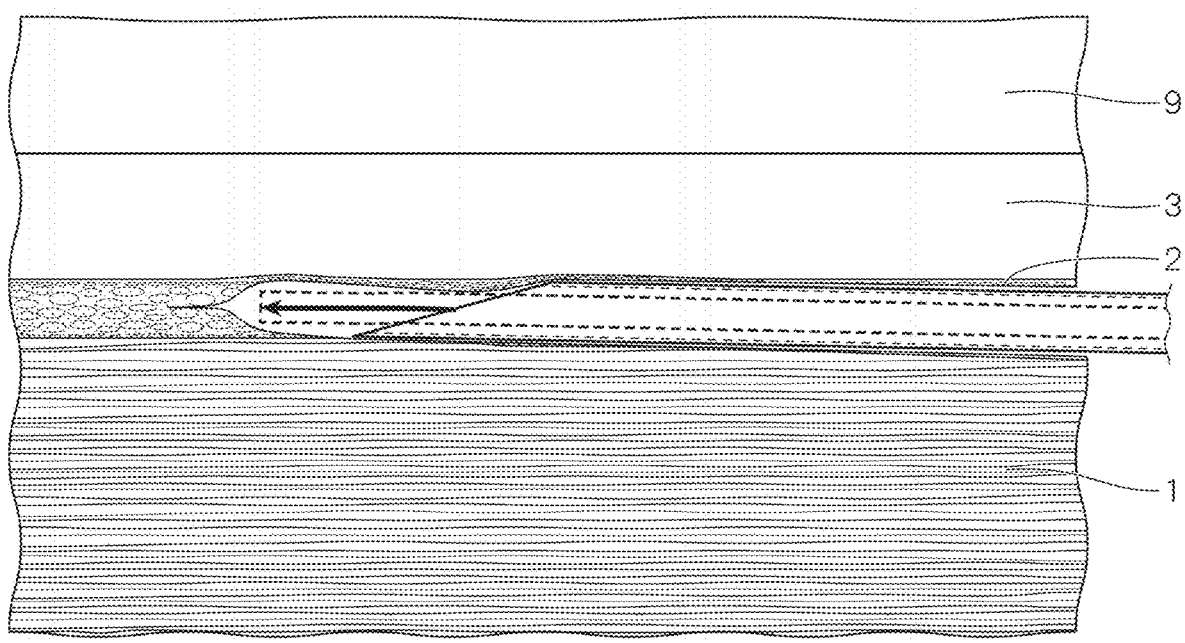
FIG. 11 is an enlarged schematic diagram illustrating a state in which one end of the tube for drug injection is inserted into the choroid through an inlet of the tip of the injection needle in a method for self-treatment according to an aspect of the present invention.

Next, as illustrated in FIG. 11, the tube is inserted into the choroid through the inlet of the tip of the injection needle. As described above, by inserting the tube into the choroid, it is possible to inject the drug solution (anti-inflammatory agent, antibiotic agent, antibody preparation, etc.) into the choroid through the tube. This makes it possible to safely and repeatedly inject a drug solution into the choroid in an amount appropriate for the state of a retinal or choroidal disease in the vicinity of the optic disc.

Note that, after insertion of the tube, the injection needle, the plunger, and the inner stabilizer are removed from the eye, and the conjunctiva is sutured in a state in which the end (opening) of the tube that is not placed in the choroid is plugged and exposed from the skin. As the inner plug, for example, 3-0 nylon having a length of 1 mm can be used.

As described above, according to the method for self-treatment of posterior segment eye disease according to an aspect of the present invention, it is possible to insert a tube into the choroid in the vicinity of the optic disc, as shown in FIG. 11, without performing intraocular surgical procedure.

Figure 12:
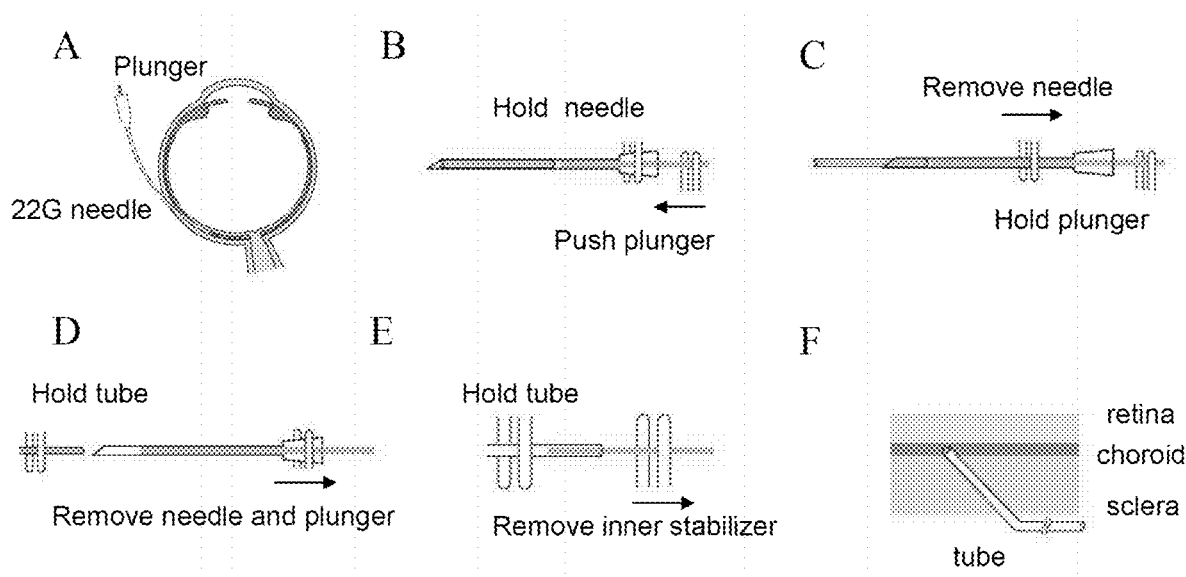
FIG. 12 is a schematic diagram illustrating an example of the step of placing one end of the tube for drug injection into the choroid in a method for self-treatment according to an aspect of the present invention.

FIG. 12 schematically shows an example of an inserting step of the tube.

In the inserting step of the tube, the tip of the injection needle is advanced in parallel within the choroid (FIG. 12A); and the inlet of the injection needle is inserted into the choroid, and then the tube (and 3-0 nylon) is inserted into the choroid from the tip of the injection needle by pressing the plunger (No. 1 nylon) with the right hand while fixing the injection needle with the left hand, for example, using tweezers or the like (FIG. 12B).

The injection needle is removed from the choroid and the sclera while fixing the plunger (No. 1 nylon) so that the tube (and the 3-0 nylon thread) remains in the choroid (FIG. 12C). The injection needle is removed from the tube together with the No. 1 nylon while fixing the tube so that the tube (and the 3-0 nylon thread) remains in the choroid (FIG. 12D).

The tube is then fixed to withdraw the 3-0 nylon as an inner stabilizer from the tube (FIG. 12E), and only the tube is placed in the choroid (FIG. 12F). As a result, one end of the tube opens within the choroid, and the other end of the tube opens in the vicinity of the incised conjunctiva. The end of the tube is inserted into the choroid in a state in which the main body of the tube extends between the conjunctiva and the sclera from the vicinity of the incised conjunctiva, and passes through the sclera in the vicinity of the optic disc.

An injection needle having a size of 32G is inserted into the end (opening) of the tube exposed outside the skin, and a drug solution is injected into the choroid through this injection needle having a size of 32G.

In this manner, by inserting the tube into the choroid, it is possible to repeatedly inject a suitable amount of the drug solution into the choroid many times at an arbitrary timing appropriate for the disease state of the posterior segment eye. Since the drug can be repeatedly injected through the tube, the amount of drug can be adjusted (i.e., increased or decreased) taking account of the state of the disease, and it is possible to maintain the drug at the effective dose for a long time. Also, under the guidance of the physician, the patient him/herself can inject the drug into the choroid through the inserted tube. For example, a microinfusion pump about 2 cm in size can be connected to the tube and implanted at the side of the outer canthus, and the amount and speed of the drug solution can be transmitted wirelessly (e.g., via Bluetooth) to the implanted pump using an application installed on a PC or other device according to the symptoms in the posterior eye segment, and the drug solution can then be injected into the choroid as appropriate.

It is also preferable to provide a valve on the outside of the tube (e.g., at the end of the tube). When a valve is provided to the tube, it is possible to prevent a situation in which the tube is easily removed from the choroid. Such a valve may be formed by diagonally forming one shallow cut or a plurality of shallow cuts in the outer wall surface of the end of the tube from the rear side, for example. It is possible to prevent the backward flow of the drug solution by providing a valve inside the tube.

It is also possible to facilitate observation of the state of the tube during fundus observation by putting a graded scale on the tube and/or coloring the tube. A micropump may be connected to the skin-side end of the tube so that a drug can be released in a sustained manner.

Furthermore, it may be useful to cover the skin-side end of tube by silicone plate or the like for fixing the tube and avoiding infections.

In one embodiment, the step (d) contains the step of (d-0) placing an implant having a magnet (hereinafter referred to as a "magnet implant") in a scleral pocket or suprachoroidal space.

This enables drug delivery to transport drugs to specific sites using magnetic force. Specifically, by injecting a drug delivery carrier holding a drug and a magnetic substance through a tube inserted into the choroid in the steps (d-1) to (d-5), the magnetic substance in the carrier is attracted to the magnet in the scleral pocket or suprachoroidal space, thereby raising the drug concentration locally at the target site in the choroid, improving the therapeutic effect at the target site, and reducing side effects at sites other than the target site.

As the magnet contained in the implant, a permanent magnet can be used. It is preferable to use a neodymium magnet because of the strength of the magnetic force and the ease of availability.

As a carrier for drug delivery, a carrier which is generally used in the field of drug delivery can be used without any particular limitation as long as it can hold a drug and a magnetic substance. For example, liposomes, lactic acid-glycolic acid copolymers, and the like can be used.

As the magnetic substance, for example, iron nanoparticles, iron oxide nanoparticles, or the like can be used.

The method of placing the magnet implant in the scleral pocket may be any method as long as the pocket is made by incising a target position on the sclera, and the magnet implant is placed in the pocket, and is not limited to the specific matters described in the following embodiments and Examples.

For example, the following method can be used. First, under an operating microscope, a fomix-based conjunctival flap was made at the inferior site. Next, a scleral incision of the half thickness was made 3 mm parallel to and 6 mm posterior to corneal limbus. Subsequently, a 25-gauge MVR blade was moved ahead in parallel to the surface of the sclera and also moved in left and right directions, thereby creating a pocket made of an incision of 3 mm×3 mm. Finally, a magnet implant is inserted into this pocket.

The method of placing the magnet implant in the suprachoroidal space may be any method as long as the magnet implant is placed in the suprachoroidal space, and is not limited to the specific matters described in the following embodiments and Examples. For example, the method described in Examples is used. In Examples, a rabbit is used, but the method is also applicable to humans.

[(e) Under a Remote Guidance of the Physician, the Patient Injects a Drug into the Choroid Through the Tube Inserted into the Choroid]

In the method for self-treatment of posterior segment eye disease according to an aspect of the present invention, the step (e) is performed by injecting a drug into the choroid by the patient him/herself under the remote guidance of the physician through the tube inserted, thereby self-treating eye disease. Thus, eye disease can be treated even remotely.

EXAMPLES

Hereinafter, the present invention will be described in detail with reference to specific examples, but the present invention is not limited to the following Examples.

(Experimental 1) Recording of Self-Fundus Image

Five subjects obtain their self-fundus image (SFI) as follows. Then, the obtained SFI was evaluated.
(i) Obtainment of SFI
 (1) a pupil was dilated by topical administration of 0.5% tropicamide.
 (2) two smartphones were prepared. One was used as a fundus videography camera (smartphone A). The other was used as a monitor that output an image captured by the camera of the smartphone A (smartphone B). The smartphone B was placed at a position where the subject can focus the camera of the smartphone A while checking the image captured by the camera of the smartphone A in the step (3) described later
 (3) the subject placed a 20D lens approximately 5 cm in front of his/her eye.
 (4) the subjects held the smartphone A so that his/her fundus could be recorded through the 20D lens and focused the camera of the smartphone A on his/her fundus while checking on the smartphone B.
 (5) the subject recorded a video of his/her fundus with the camera of the smartphone A
 (6) the subject obtained SFI by selecting a still image from the video by screenshot.
(ii) Evaluation of SFI
For five subjects, clear self-fundus images as shown in FIG. 2 could be obtained.

Thus, by using two smartphones and 20D lens, self-fundus images can be obtained by a simple operation without requiring an expensive device.

(Experimental 2) Self-Diagnosis of Posterior Segment Eye Disease

The prepared fundus image was provide into an automatically constructed deep-learning model to determine whether or not the vitreous opacity was found to evaluate the method for self-diagnosis.
(i) Automatic Construction of Deep-Learning Model
Fundus images were obtained from patients with informed consent. A fundus camera ("VX-10," manufactured by Kowa Company, Limited) was used to obtain fundus images.

Based on the judgment of the ophthalmologist, 24 fundus images were divided into two groups: 12 control group (mean age, 57.6±19.7 years old) and 12 vitreous opacity group (mean age, 63.5±9.9 years old). The classified fundus images were provided to the neural architecture search framework of AutoML in Google Cloud, the fundus images of the control group were tagged as "not vitreous opacity", and the fundus images of the vitreous opacity group were tagged as "vitreous opacity," and the deep-learning model was automatically constructed.
(ii) Determination of Vitreous Opacity
In addition to the 24 fundus images used to construct the model, 10 fundus images were prepared. These 10 fundus images were determined by an ophthalmologist in advance, and composed of 5 control group and 5 vitreous opacity group.

An automatically constructed deep-learning model was used to determine whether each of the 10 fundus images was vitreous opacity.
(iii) Evaluation of Method for Self-Diagnosis
The automatically constructed deep-learning model was able to determine whether each of the 10 fundus images was vitreous opacity with 100% sensitivity, 100% specificity, and 100% accuracy. The results indicate that this model is useful for the diagnosis of posterior segment eye diseases including vitreous opacity, and that it is possible to determine whether or not the patient has a posterior segment eye disease by using an automatically constructed deep-learning model not only by medical personnel but also by patients.

Combined with the recording of the self-fundus image described above, the patient can accurately determine whether or not the patient has a posterior segment eye disease with a simple operation without requiring an expensive device by using his/her own obtained self-fundus image and using the automatically constructed deep-learning model.

(Experimental 3) Self-Treatment of Posterior Segment Eye Disease

In order to investigate the effectiveness of the method for self-treatment of posterior segment eye disease according to an aspect of the present invention, whether the injection of dexamethasone (DEX) into the choroid through a tube suppresses inflammatory vitreous opacity due to endotoxin-induced uveitis was examined in a rabbit model.

(i) Fabrication of Tube Insertion System

A silicon tube (0.4 mm outer diameter, 0.3 mm inner diameter, manufactured by ARAM Corporation), an inner stabilizer (3-0 nylon resin, manufactured by Akiyama-sei-sakusyo. Co., Ltd.), a plunger (No. 1 nylon resin, manufactured by Alfresa Pharma Corporation), and a Terumo needle 22G (manufactured by Terumo Corporation) were used to fabricate a tube insertion system into the choroid as shown in FIGS. 3 and 4.

(ii) Insertion of Tube into Choroid

All experiments were conducted in accordance with ARVO Statement for the Use of Animals in Ophthalmic and Vision Research and the Guidelines for Experimental Animals at Iwate Medical University. Three-month-old Japanese white rabbits (purchased from KITAYAMALABES CO., LTD.) weighing 2 to 2.5 kg were used. Since these rabbits have a pigmentless retinal pigment epithelium (RPE), the choroidal vessels of the fundus can be easily observed with an ophthalmoscope.

Figure 13:
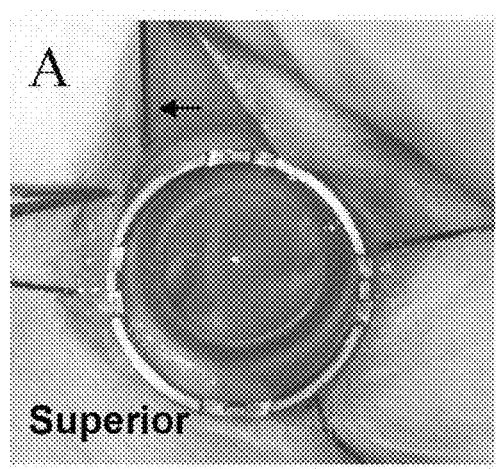
FIG. 13 shows a photograph of the step of placing one end of the tube for drug injection into the choroid in Example.
Figure 13:
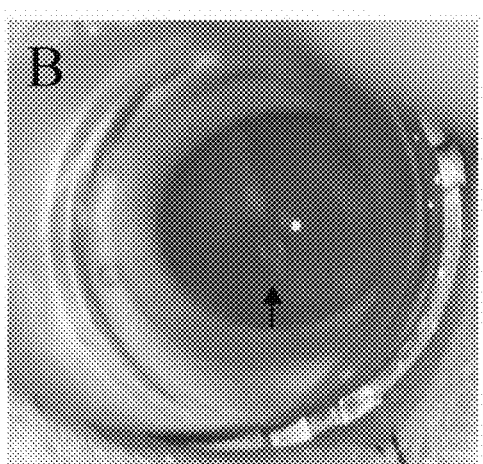
Figure 13:
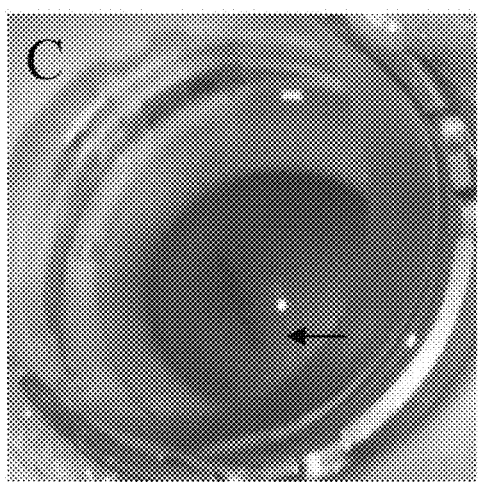
Figure 13:
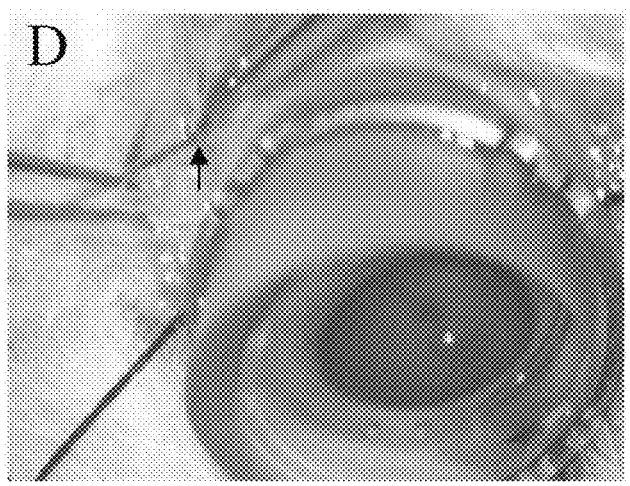

Rabbits were anesthetized with ketamine hydrochloride (24 mg/kg) and xylazine hydrochloride (6 mg/kg). The eye surface was then anesthetized with topical instillation of 2% xylocaine. The pupil was dilated with topical 0.5% tropicamide. The conjunctiva was incised 2 mm parallel from the inferior limbus to expose the sclera. A 22G needle was then inserted into the subconjunctiva (FIGS. 7, 12A, and 13A) and the sclera was pressed to confirm the insertion site near the optic disc. The tip was pierced shallowly into the sclera and advanced parallel to the choroid at half the choroid thickness (FIGS. 8 to 10 and 13B). The plunger was then pushed and the tube was inserted into the choroid until the tip of the tube reached two papillary diameters below the optic disc (FIGS. 11 and 13C). Thereafter, the 22G needle, the plunger, and the inner stabilizer were removed (FIGS. 12B to E and 13D), and the tube inserted near the optic disc was observed by fundus test. Mild choroidal hemorrhages were observed throughout most of the experiments, and these hemorrhages resolved spontaneously within 1 week. In addition, the tip of tube on the conjunctival side was guided to a position of 5 mm from the outside of the external eye region using the 22G needle, and the tube was exposed on the skin through the subconjunctiva and subcutaneous.

To evaluate possible side effects of tube insertion into the choroid, the treated eyes were extracted after euthanasia on day 14 and evaluated by histopathology.

(iii) Uveitis Induction and Surgical Procedures

Figure 14:
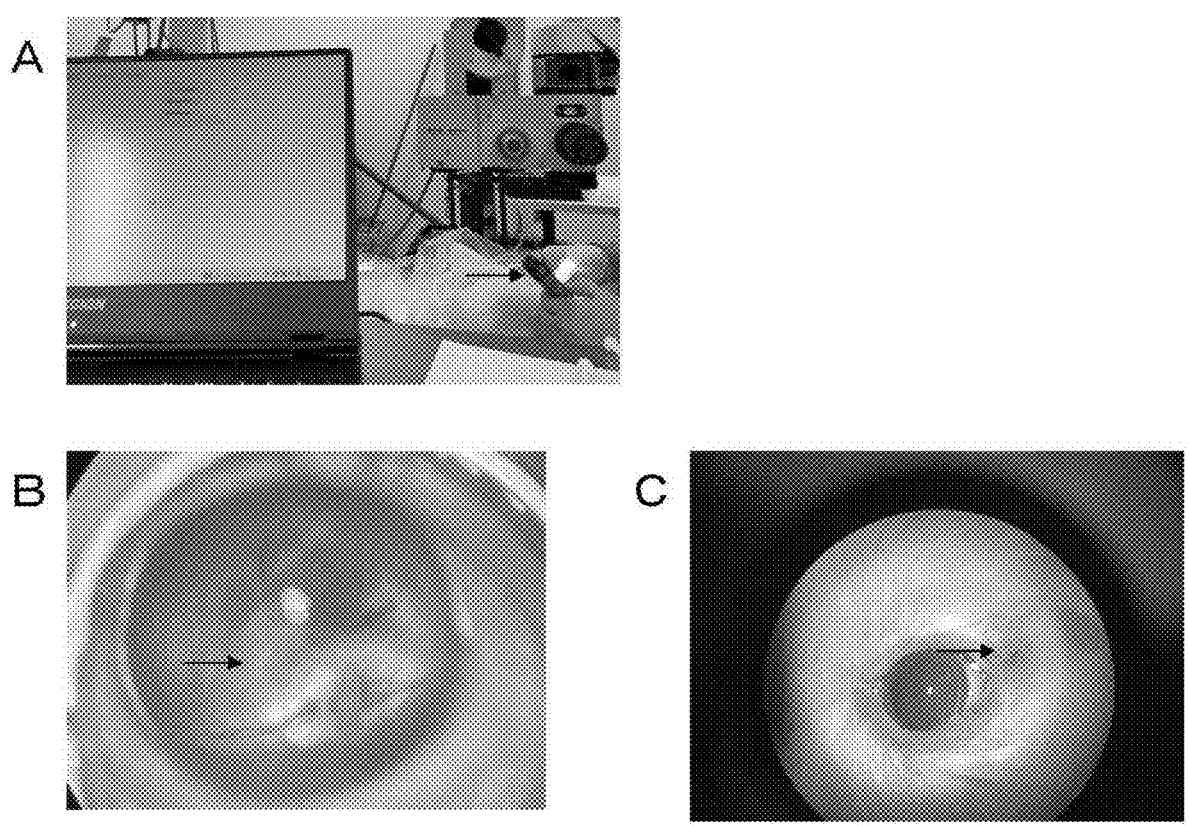
FIG. 14 shows a photograph of the step of injecting the drug into the choroid by an injector via the tube for drug injection inserted in Example.

After the tube insertion, endotoxin-induced uveitis (HU) was induced in 8 rabbits (8 eyes) by lipopolysaccharide (LPS) derived from *Escherichia coli* (manufactured by Sigma-Aldrich Co. LLC). 100 ng of LPS solution was injected into the vitreous body using a 27G needle at a 12 o'clock position, 3 mm posterior to the corneal limbus. The solution contained indocyanine green (ICG) (50 µg/µL). The diffusion state of the LPS solution in the vitreous body was observed by ophthalmoscope using ICG. A dose-response study was conducted in advance to confirm that 100 ng was optimal for the induction of uveitis in rabbits. Since maximal inflammatory symptoms were seen 2 days after injection, inflammatory vitreous opacity was evaluated 2 days after injection by ophthalmological observation and vitreous humor protein measurement. The amount of DEX injected was entered into the application and the amount of DEX was determined on the computer. The data on the quantity of DEX was then transmitted to a wireless injector ("Tofuty", manufactured by ICOMES LAB Co., Ltd.). Subsequently, DEX solution (100 µg/100 µL) was simultaneously injected into four eyes from the tube on the skin-side using the wireless injector (FIG. 14A). This solution contained ICG (50 µg/µL), which was used for ophthalmoscopic clarification of the wide diffusion range of DEX in the choroid. When DEX solution containing ICG was administered to the choroid immediately after LPS injection, ICG staining was observed at the inferior site of the fundus around the tube (indicated by arrows, FIG. 14B). ICG staining was also observed in the vitreous body because LPS solution containing ICG was injected into the vitreous body.

The remaining four eyes, which were injected LPS only and no DEN served as controls.

After the procedure, the tip of the tube was suture-fixed onto the skin to repeatedly inject DEX (FIG. 14C).

(iv) Clinical Observation and Protein Measurement of Vitreous Humor in Inflammatory Vitreous Opacity Model Due to Rabbit Uveitis.

On day 2, arbitrary observer evaluated the severity of inflammation and vitreous opacity using slit-lamp microscopy and fundus test. Vitreous opacity was graded from 0 to 4 (0=no inflammation, +1=mild opacity of retinal vessels and optic nerve, +2=moderate opacity of the optic disc, +3=marked opacity of the optic disc, +4=no visible optic disc, or visibility of the posterior pole was prevented by corneal swelling) by test of the posterior pole and optic nerve visibility.

For protein measurements, four eyes in each group were used on day 2 after procedure. Vitreous humor was collected from the eyes of each rabbit and centrifuged at 250×g for 5 min, and protein measurement was performed using the supernatant. The protein content of vitreous humor was determined using a Bio-Rad assay kit with bovine serum albumin as a standard-dilution reference curve.

(v) Statistical Analysis

Statistical analysis was performed by U-test of Mann-Whitney. P values of less than 0.05% were considered significant differences.

(vi) Evaluating Efficacy of Method for Self-Treatment

Figure 15:
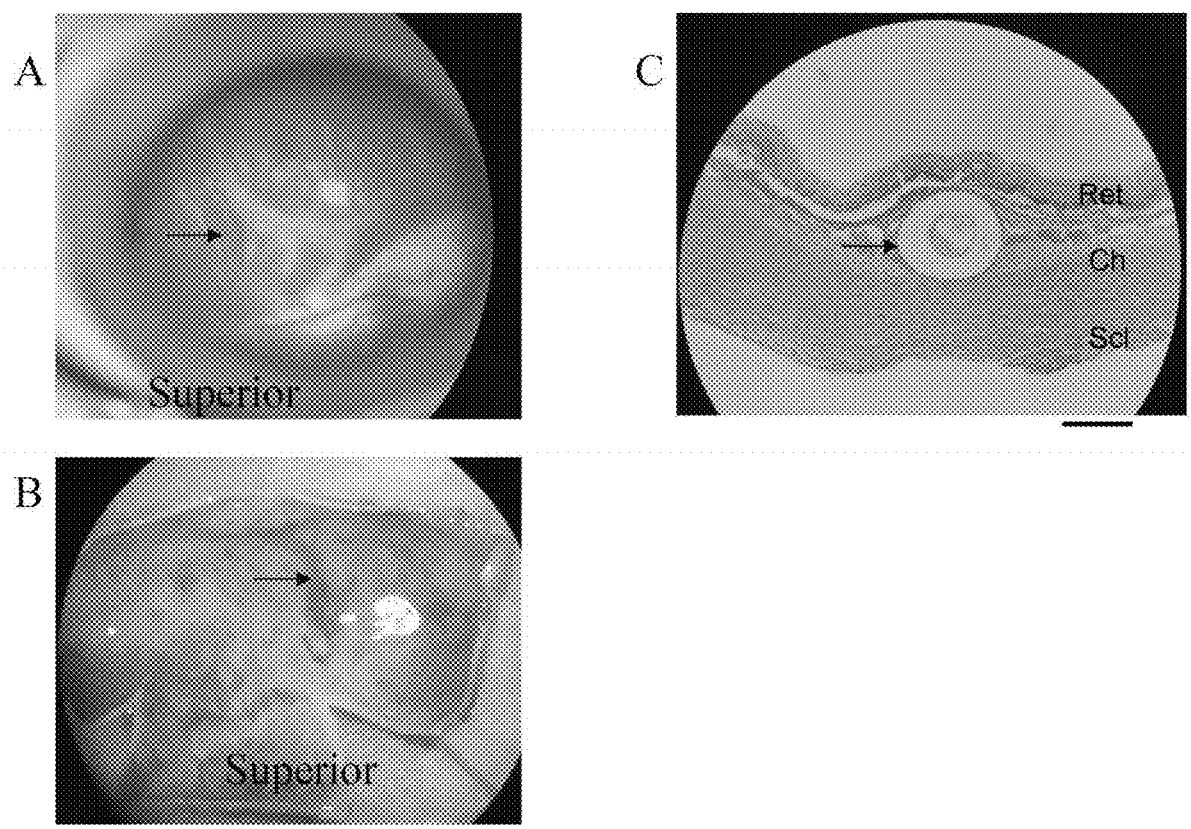
FIG. 15 shows a representative photograph taken two weeks after insertion of the tube for drug injection in Example (scale bar: 250 micrometers, Ret retina, Ch: choroid, Scl: sclera).

Histopathological test revealed that the tube in the choroid was still visible at the site of insertion even 14 days after procedure (arrows, FIGS. 15A and B). In the retina, disappearance of the photoreceptor outer segment and the outer granular layer corresponding to the site of the tube inserted was observed (FIG. 15C). No abnormalities were observed in the retina other than the site of the tube inserted.

Figure 16:
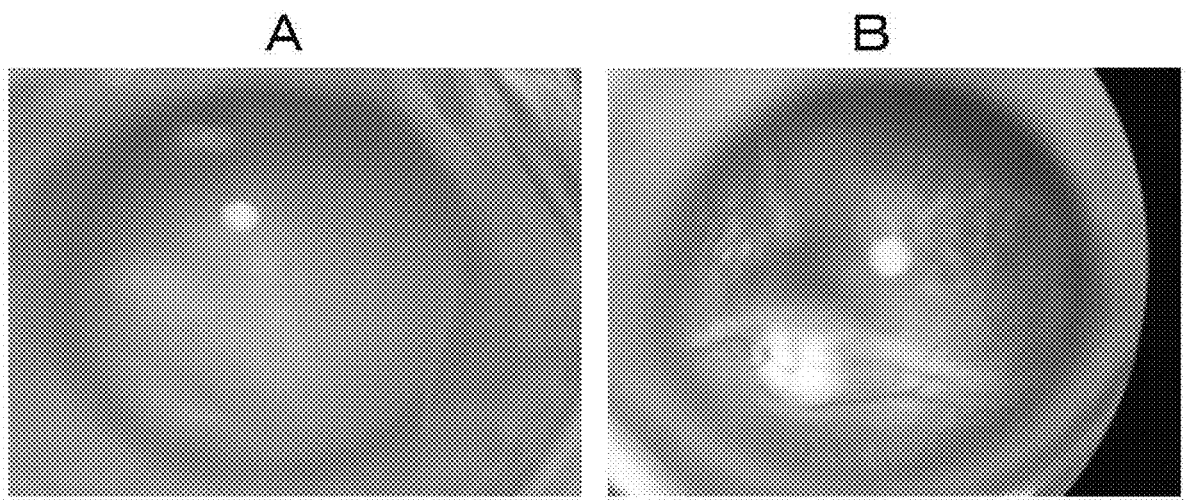
FIG. 16 shows a representative photograph taken 2 days after injection of lipopolysaccharide in Example.

Clinical grading on day 2 was 3.25±0.96 in the control group (FIG. 16A) and 0.75±0.96 in the DEX group (FIG. 16B). The clinical score of the DEX group was significantly lower than that of the control group on day 2 ($p<0.05$) (FIG. 16). Therefore, this data indicates that DEX injection through the tube effectively reduces vitreous opacity in EIU.

Since EIU increases protein levels in aqueous humor, the inventor investigated whether DEX injection through the tube is effective in reducing proteins in vitreous humor. The protein concentration in the DEX group on day 2 was 20.5±15.0 mg/mL, whereas that in the control group was 55.3±16.0 mg/mL. Eyes in the DEX group showed a significant reduction in mean protein concentration on day 2 compared to eyes in the control group ($p<0.05$). The data also indicate that DEX injection through the tube significantly reduces the increased vitreous proteins in the EIU.

(Experimental 4) Drug Delivery by Magnet Implant

A magnet implant was placed in the suprachoroidal space to investigate whether drug delivery to the target site was possible.

(i) Placement of Magnet Implant

Three-month-old white rabbits (purchased from KITAYAMA LABES CO., LTD.) weighing 2 to 2.5 kg were used. A scleral incision was made 3 mm parallel to and 4 mm posterior to corneal limbus to expose the choroid. The tube having magnet was then inserted and placed into the suprachoroidal space (arrow, FIG. 17A).

(ii) Investigation of Drug Delivery

After placement of the tube having magnet, the iron nanoparticles were injected into the vitreous body. In addition, iron nanoparticles were injected in the same manner in the control group in which no magnet was placed.

Figure 17:
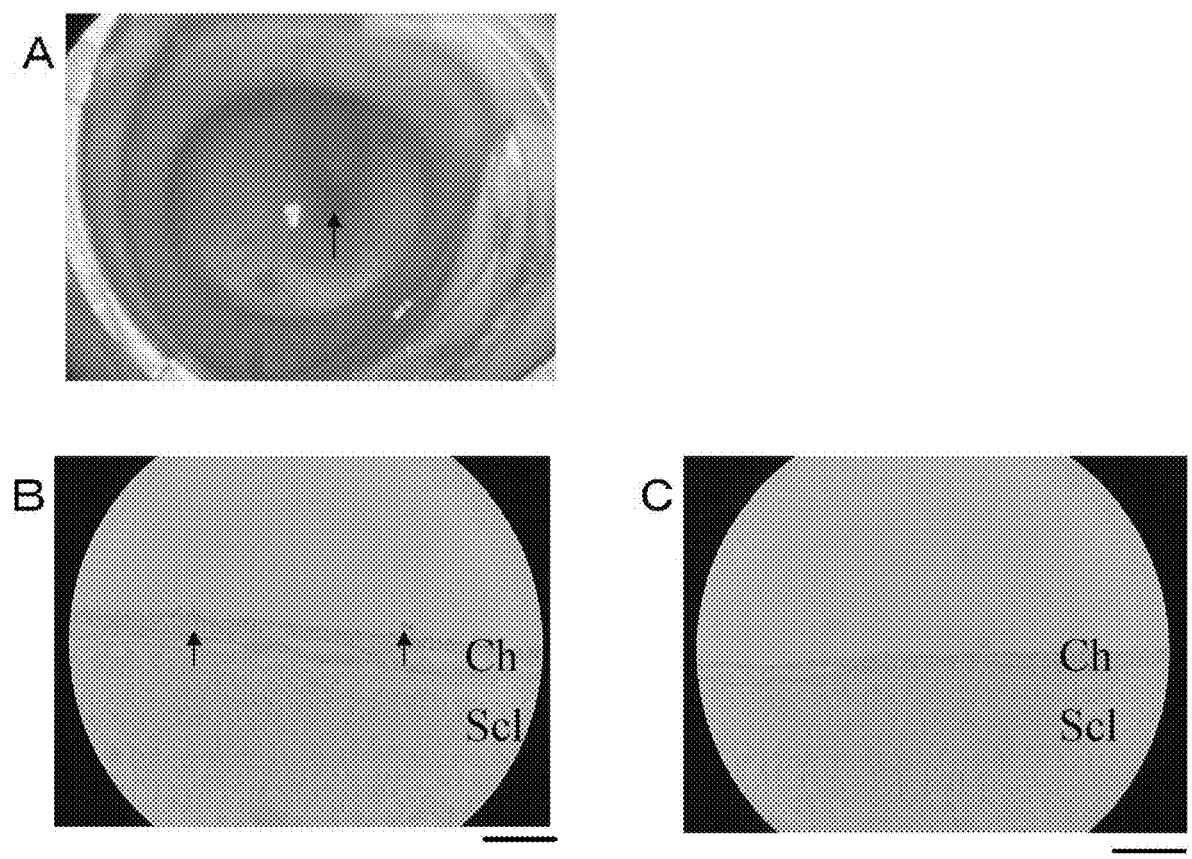
FIG. 17 shows micrographs of neodymium magnets inserted into the suprachoroidal space and iron nanoparticles attached to the choroid (scale bar: 250 micrometers, Ch: choroid, Scl: sclera).

As shown in FIG. 17, it was confirmed that iron nanoparticles adhered to the choroid in the group in which the magnet implant was placed (arrow, FIG. 17B). In the control group, no iron nanoparticles were attached to the choroid (FIG. 17C).

From these results, in the method for self-treatment of posterior segment eye disease according to an aspect of the present invention, it is possible to attract the magnetic substance in the carrier to the magnet in the suprachoroidal space or the scleral pocket by injecting the drug delivery carrier holding the drug and the magnetic substance through the tube inserted into the choroid. This can be expected to raise the drug concentration locally at the target site in the choroid, improving the therapeutic effect at the target site, and reducing side effects at sites other than the target site.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated by reference in their entirety.

DESCRIPTION OF SYMBOLS

1 Sclera
2 Choroid
3 Retina
4 Cornea
5 Iris
6 Ciliary body
7 Zonule of Zinn
8 Crystalline lens
9 Vitreous body
10 Aqueous humor

The invention claimed is:

1. A method for self-diagnosis of posterior segment eye disease, comprising:
(a) a patient obtains a self-fundus image; and
(b) the patient provides the self-fundus image into an automatically constructed deep-learning model to determine whether or not the patient has posterior segment eye disease,
wherein the step (a) comprises:
(a-1) the patient instills mydriatic drops to dilate his/her pupil;
(a-2) the patient places a monitor that outputs an image captured by a fundus videography camera;
(a-3) the patient places a lens in front of his/her eye;
(a-4) the patient holds the camera so that the fundus can be recorded through the lens and focuses the camera on the fundus of his/her eye while checking the monitor;
(a-5) the patient records a video of his/her fundus with the camera; and
(a-6) the patient obtains a self-fundus image as a still image from the video.

2. The method for self-diagnosis according to claim 1, wherein the posterior segment eye disease is selected from the group consisting of vitreous opacity, diabetic retinopathy, macular degeneration, retinal vein occlusion, and uveitis.

3. The method for self-diagnosis according to claim 1, wherein the camera is a smartphone or tablet computer.

4. The method for self-diagnosis according to claim 1, wherein the monitor is a smartphone or tablet computer.

5. The method for self-diagnosis according to claim 1, wherein in the step (b), fundus images obtained from the patient with the posterior segment eye disease and fundus images obtained from the patient without the posterior segment eye disease are provided into an exploration framework of neural architecture to automatically construct a deep-learning model.

6. A method for self-treatment of posterior segment eye disease, comprising:
(d) in a clinic, the physician places one end of a tube for drug injection in a choroid of the patient diagnosed as having posterior segment eye disease by the method for self-diagnosis according to claim 1 and exposes the other end of the tube outside a skin of the patient; and
(e) under a remote guidance of the physician, the patient injects a drug into the choroid through the tube inserted into the choroid,
wherein the step (d) comprises:
(d-1) incising a conjunctiva, and inserting an injection needle between the conjunctiva and a sclera;
(d-2) advancing a tip of the injection needle to a vicinity of an optic disc along a surface of the sclera, placing a lens over a cornea so that a fundus can be observed, and observing the tip of the injection needle that can be observed as a white raised portion of the sclera while pressing the sclera using the tip of the injection needle and observing the fundus through the lens;
(d-3) moving the tip of the injection needle to determine an appropriate insertion position of the tube in the vicinity of the optic disc;
(d-4) inserting the tip of the injection needle diagonally into the sclera, advancing the tip of the injection needle into the choroid, and inserting the one end of the tube into the choroid through an inlet of the tip of the injection needle; and
(d-5) placing the one end of the tube into the choroid and pulling out the injection needle.

7. The method for self-treatment according to claim 6, wherein the step (d) comprises:
(d-0) placing an implant having a magnet in a scleral pocket or suprachoroidal space.

* * * * *